United States Patent [19]
Gould et al.

[11] Patent Number: 5,062,303
[45] Date of Patent: Nov. 5, 1991

[54] ENCAPSULATED ACTUATOR FOR TESTING OF SPECIMENS

[75] Inventors: Larry D. Gould, Canaan; David M. Cole, Lyme, both of N.H.

[73] Assignee: The United States of America as represented by the Secretary of the Army, Washington, D.C.

[21] Appl. No.: 542,331

[22] Filed: Jun. 22, 1990

[51] Int. Cl.⁵ .............................................. G01N 3/00
[52] U.S. Cl. .................................................... 73/798
[58] Field of Search ................. 73/825, 798, 819, 837, 73/807, 816, 794, 795, 796, 797

[56] References Cited

U.S. PATENT DOCUMENTS 4,679,441 7/1987 Johnson et al. .................... 73/825 X

FOREIGN PATENT DOCUMENTS 813186 3/1981 U.S.S.R. ................................. 73/825

Primary Examiner—Jerry W. Myracle
Attorney, Agent, or Firm—Darrell E. Hollis

[57] ABSTRACT

An encapsulated actuator for testing specimens includes a housing containing a wall defining first and second chambers. The specimen under test is arranged in one of the chambers and vent holes are provided in the wall in order to equalize the pressure within the chambers. An actuator is arranged in the second chamber for generating a mechanical force and a force transmitting device is connected between the actuator and the specimen. The force transmitting device passes through an opening in the housing wall and transmits the mechanical force from the actuator to the specimen. Because the actuator is encapsulated within the housing, it is subjected to the same confining pressure as the specimen.

16 Claims, 3 Drawing Sheets

ENCAPSULATED ACTUATOR FOR TESTING OF SPECIMENS

STATEMENT OF GOVERNMENT INTEREST

The invention described and claimed herein may be manufactured and used by or for the Government of the united States of America for governmental purposes without the payment of royalties thereon or therefor.

BACKGROUND OF THE INVENTION

The present invention relates to a low friction actuator used to apply an independent axial stress along one axis of a specimen which is subjected to a high confining pressure within a pressurized chamber.

BRIEF DESCRIPTION OF THE PRIOR ART

In previously known test chambers, it is typical for a piston rod to pass through the wall of the confining chamber in order to transmit loads from an external actuator to the enclosed specimen. Such an arrangement necessitates a high pressure seal at the wall of the confining chamber where the piston rod enters.

This arrangement presents a number of problems. Due to the high confining pressure of the chamber, the force necessary to maintain the proper seal creates significant drag on the piston rod. This, combined with the inherent drag of the piston itself, results in an unacceptable condition. In addition, in creep testing, where the specimen deforms slowly under a constant force, irregular piston movement, commonly known as stick-slip, occurs. This results in piston advance in a series of irregular steps instead of the desired smooth continuous advancement. While this phenomenon can be minimized through the use of sophisticated actuators incorporating special rings, seals and lubrication, this can be very expensive and is not always successful. In testing material at extremely low temperatures, such sealing and lubrication problems greatly increase.

The present invention was developed in order to overcome these and other drawbacks of the prior art by providing an improved system for axial creep testing of a specimen subjected to elevated hydrostatic pressure in a pressurized encapsulated actuator.

SUMMARY OF THE INVENTION

According to the invention, a pressurized test chamber is designed to receive a cylindrical specimen and subject it to an elevated all-around confining pressure while applying an additional axial stress. The test chamber is designed so that the actuator used to apply the axial stress is "encapsulated" within the chamber and, therefore, subjected to the same confining pressure as the specimen.

The test chamber is constructed of two separate chambers, aligned vertically and connected via vent holes to equalize the confining pressure within the chambers. The test specimen is placed in the lower chamber and a piston rod, which passes through the mating wall between the chambers, is placed in contact with the specimen. A monitoring load cell is positioned beneath the specimen, and other instrumentation to measure sample deformation and the like is attached to the specimen.

An actuator is positioned in the upper chamber and is used to impart a downward axial stress on the specimen via the piston rod. The actuator is placed under the same confining pressure as the specimen via the vent holes. Suitable actuators include rolling diaphragm type hydraulic actuators, conventional sealed piston hydraulic actuators, dead weights, and electro-mechanical actuators such as precision screw-jacks.

BRIEF DESCRIPTION OF THE FIGURES

Other objects and advantages of the present invention will become apparent from a study of the following specification when viewed in the light of the accompanying drawing, in which.

DETAILED DESCRIPTION

Figure 1:
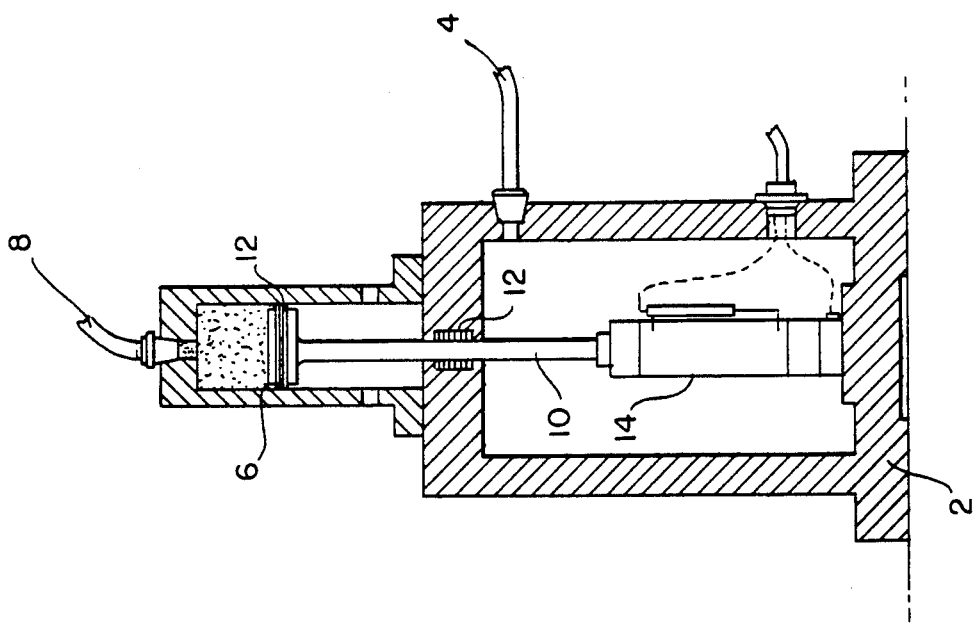
FIG. 1 is a front sectional view of a test chamber of the prior art where the actuator is isolated from the elevated confinement pressure.

FIG. 1 illustrates a prior art approach to placing a cylindrical specimen under axial stress while simultaneously subjecting it to a high confining hydrostatic pressure. A test chamber 2 is used to house the specimen 14 and place it under an elevated confining pressure via a pressure line 4. An actuator piston 6 is pressurized via an actuator pressure line 8 to place an axial stress on the specimen via a piston rod 10. High pressure seals 12 are provided within the piston cylinder and in the upper wall of the test chamber where the piston rod passes through the chamber wall. These high pressure seals are expensive to design and manufacture to exact tolerances and induce an undesirable intermittent piston movement during creep testing, commonly known as stick-slip. They also introduce a significant drag on the piston due to the force required to maintain a proper seal.

Figure 2:
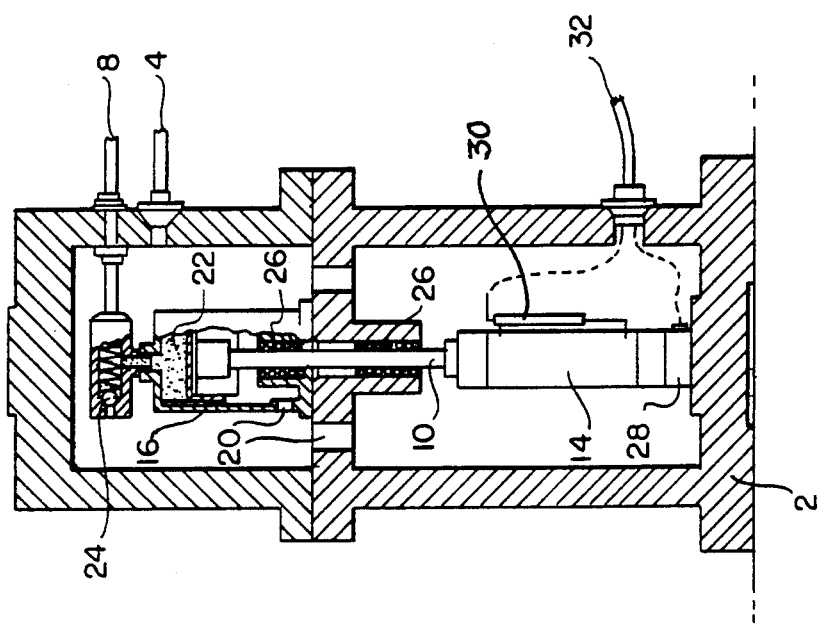
FIG. 2 is a front sectional view of a first embodiment of the invention using a rolling diaphragm type actuator.

A first embodiment of the invention, as illustrated in FIG. 2, utilizes a similar pressurized test chamber 2 to hold the test specimen 14. The actuator 16 is encapsulated within an upper chamber 18 which has an internal confining pressure equalized to that of the test chamber 2 via vent holes 20. The actuator illustrated in FIG. 2 is a rolling diaphragm type piston. The differential pressure is initially equalized across the diaphragm 22 of the actuator via a check valve 24 and the vent hole 20. This is particularly important in a rolling diaphragm actuator since the diaphragm in such a device can withstand a relatively small differential pressure before rupturing. Typical pressure limitations are on the order of 150 psig (1 Mpa). The elevated confinement pressure of the preferred embodiment, by contrast, is on the order of 3000 psig (20 Mpa). For this reason, previous high pressure test chambers did not use rolling diaphragm type actuators.

After the differential pressure is equalized, actuator pressure is introduced via the pressure line 4. This additional pressure is prevented from entering the test chamber by the check valve 24. An axial force is imparted to the specimen 14 via the piston rod 10. This force is equal to the net cross-sectional area of the piston multiplied by the differential pressure. Thus, high forces are attainable by increasing the size of the actuator, despite the limitation in diaphragm differential pressure discussed above. The piston rod 10 is guided by low friction bearings 26 such as precision linear ballbushings which assure axial alignment.

A load cell 28 is positioned under the specimen and a sensor 30 is provided to measure sample deformation. All instrumentation wires 32 are routed through the test chamber wall via specially designed high pressure electrical connectors.

Figure 3:
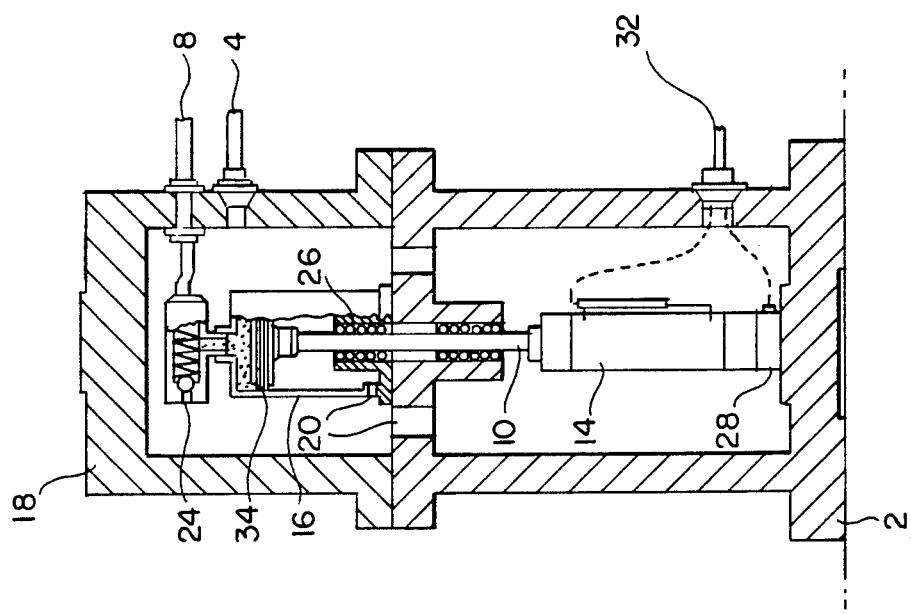
FIG. 3 is a front sectional view of a second embodiment of the invention using a conventional sealed piston actuator.

FIG. 3 illustrates a second embodiment of the invention. Instead of a rolling diaphragm type actuator, a conventional hydraulically actuated piston 34 with ordinary pressure actuated seals is used to drive the piston rod 10. While the piston seal does present some drag, the drag is greatly reduced due to the large decrease in differential pressure across the seal and the elimination of the piston rod seal. Again, differential pressure in this embodiment is approximately 1 MPa vs 20 MPa in the prior art embodiment of FIG. 1.

Figure 4:
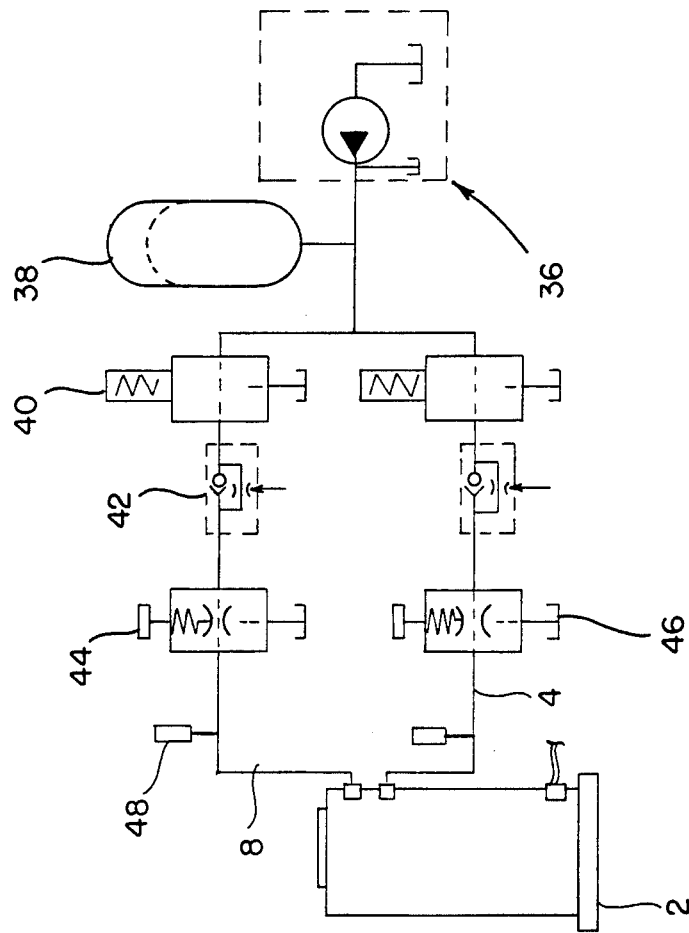
FIG. 4 is a circuit diagram of the hydraulic system of the invention.

The overall hydraulic system is shown in FIG. 4. A single hydraulic fluid pressure source comprising a hydraulic power unit 36 and an accumulator 38 is used to generate both the confinement pressure for the test chamber 2 and the actuator pressure through parallel pressure lines 4 and 8, respectively, incorporating conventional main control valves 40, flow control valves 42, pressure regulators 44 and 46, and pressure tranducers 48.

Figure 5:
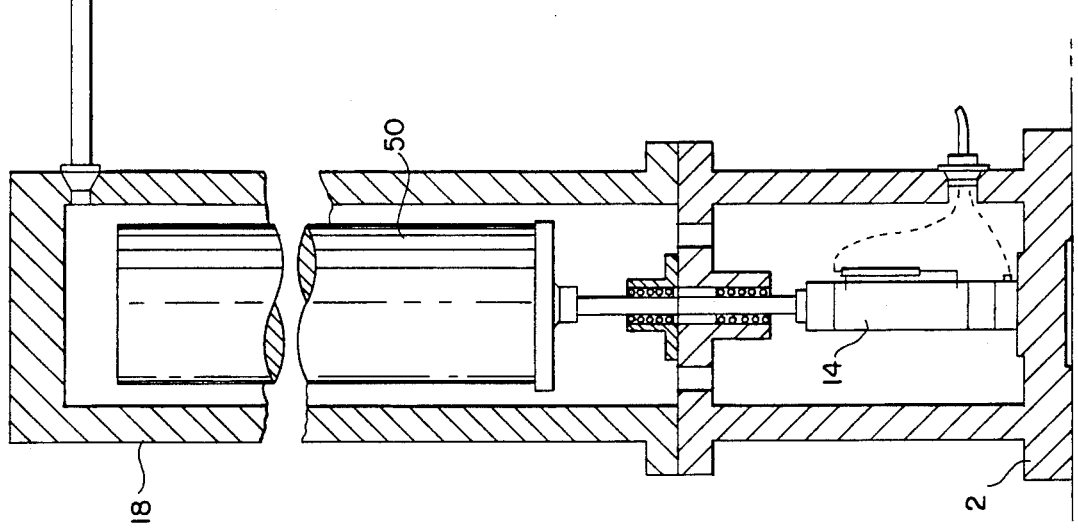
FIG. 5 is a front sectional view of a third embodiment of the invention incorporating a dead weight actuator.

FIG. 5 illustrates a third embodiment of the invention using a dead weight 50 as the actuator. By placing the dead weight in the pressurized chamber, and thus eliminating the requirement for high pressure seals, any stick-slip problem due to seal drag is eliminated.

Figure 6:
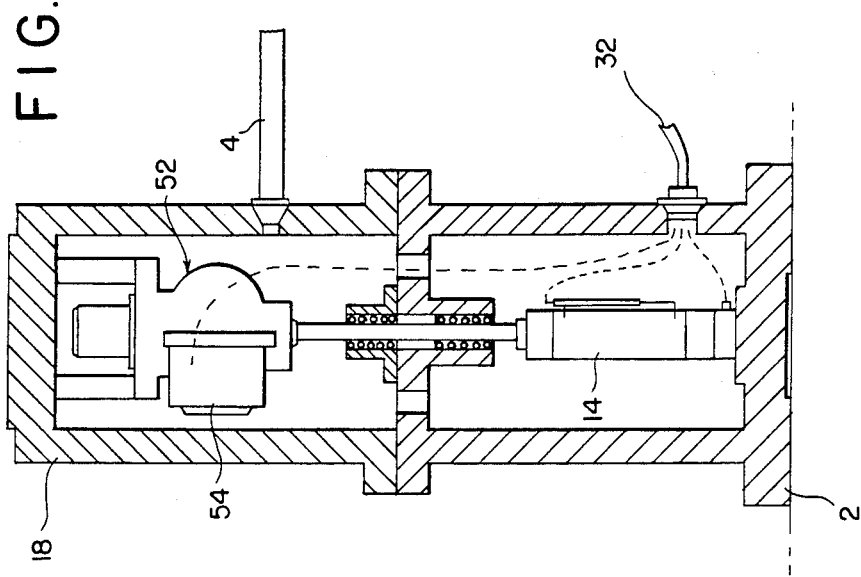
FIG. 6 is a front sectional view of a fourth embodiment of the invention incorporating a precision electro-mechanical screw jack as the actuator.

FIG. 6 illustrates a fourth embodiment of the invention. In this embodiment, a precision electro-mechanical screw-jack 52 is used as the actuator. A stepping motor 54, driven by an external power supply connected via leads 32, drives the screw-jack 52 to place an axial load on the specimen 14. Again, high pressure dynamic seals are eliminated in this arrangement. This type of stepped electro-mechanical actuator is best suited for applying a constant deformation rate to the specimen while the hydraulically actuated systems, and the dead weight, of course, are better suited for applying a constant load.

With the different embodiments of the present invention, an improved system for axial creep testing of a specimen subjected to elevated hydrostatic pressure in a pressurized encapsulated actuator is provided. Thus, a low pressure actuator within a high pressure chamber is characterized by reduced stick-slip in creep testing. The invention affords pressure compensation in the encapsulated actuator to enable its use in any hydrostatic environment and reduces the energy requirements relative to conventional pressurized specimen test chambers. The invention can also be adapted to apply a tensile stress to the specimen instead of a compressive stress.

While in accordance with the provisions of the patent statute the preferred forms and embodiments have been illustrated and described, it will be apparent to those of ordinary skill in the art that various changes and modifications may be made without deviating from the inventive concepts set forth above.

What is claimed is:

1. Apparatus for applying a mechanical stress to a specimen, comprising
   (a) a housing containing a wall defining first and second chambers, the specimen being arranged in said first chamber and the walls containing a plurality of vent holes to equalize the hydrostatic pressure within said first and second chambers;
   (b) actuator means arranged within said second chamber for generating a mechanical force;
   (c) force transmitting means connected between said actuator means and the specimen, said force transmitting means passing through an opening in said housing wall to transmit the mechanical force from said actuator means to the specimen, whereby said actuator is encapsulated within said second chamber and subjected to the same confining pressure as the specimen.

2. Apparatus as defined in claim 1, wherein said actuator means comprises a hydraulically actuated rolling diaphragm type piston.

3. Apparatus as defined in claim 2, and further comprising means for introducing an actuating pressure into an upper end of said actuator means above said diaphragm via an actuator pressure line to create a differential pressure across said diaphragm to generate said mechanical force.

4. Apparatus as defined in claim 3, and further comprising a check valve connected with the upper end of said actuator means and a vent hole in the lower end of said actuator means to equalize the pressure across said diaphragm prior to introduction of said actuating pressure.

5. Apparatus as defined in claim 4, wherein said confining pressure is on the order of 20 MPa while said differential pressure is on the order of 1 MPa.

6. Apparatus as defined in claim 2, wherein said confining pressure is on the order of 20 MPa while said differential pressure is on the order of 1 MPa.

7. Apparatus as defined in claim 1, wherein said actuator means comprises a conventional hydraulically actuated piston and cylinder including a lower pressure seal between the piston and cylinder.

8. Apparatus as defined in claim 7, and further comprising means for introducing an actuating pressure into an upper end of said actuator means above said piston via an actuator pressure line to create a differential pressure across said piston to generate said mechanical force.

9. Apparatus as defined in claim 8, and further comprising a check valve connected with the end of said actuator means and a vent hole in the lower end of said actuator below said piston in order to equalize the pressure across said piston prior to introduction of said actuating pressure.

10. Apparatus as defined in claim 1, wherein said force transmitting means comprises a piston rod, said piston rod being guided through said additional hole by low friction bearings to assure axial alignment with said specimen.

11. Apparatus as defined in claim 1, and further comprising a load cell placed adjacent to said specimen for monitoring the load placed on the specimen.

12. Apparatus as defined in claim 1, and further comprising a deformation sensor placed adjacent to said sample for monitoring the deformation of the specimen.

13. Apparatus as defined in claim 1, wherein said actuator comprises a dead weight.

14. Apparatus as defined in claim 1, wherein said actuator comprises an electro-mechanical screw-jack.

15. Apparatus as defined in claim 1, wherein said first and second chambers are arranged with said second chamber above said first chamber.

16. Apparatus as defined in claim 1, wherein said force is directed through an axis of the specimen to exert a compressive or tensile stress thereto.

* * * * *